United States Patent [19]

Snow

[11] 4,323,786
[45] Apr. 6, 1982

[54] SEAM DETECTION AND CONTROL SYSTEM

[75] Inventor: David H. Snow, Jackson, Mich.

[73] Assignee: Sparton Corporation, Jackson, Mich.

[21] Appl. No.: 165,541

[22] Filed: Jul. 3, 1980

[51] Int. Cl.³ .............................................. G01N 21/86
[52] U.S. Cl. .................................. 250/559; 250/223 R
[58] Field of Search ........... 250/548, 557, 561, 223 R, 250/562, 563, 571, 572, 209; 356/429, 430, 448; 226/45

[56] References Cited

U.S. PATENT DOCUMENTS 4,067,760  1/1978  Nelson ................................. 250/548
4,286,149  8/1981  Ben-Nathan et al. ........... 250/223 R Primary Examiner—David C. Nelms
Attorney, Agent, or Firm—Beaman & Beaman

[57] ABSTRACT

The invention pertains to apparatus for sensing the presence of a seam in a moving strip of fabric being proccesed, the detection of a seam actuating a control circuit which modifies the fabric processing to accomodate the seam. An optical seam detector determines the rate of movement of the fabric, initiates a electronic counter producing a voltage inversely proportional to the rate of fabric movement. An electronic timer, also initiated by the sensing of the seam, receives and evaluates the velocity determined voltage and produces a timed actuation of the fabric processing apparatus corresponding to the seam arriving at the processing station. The disclosed circuit is capable of actuating two fabric processing stations sequentially arranged in the direction of fabric movement, and the circuitry resets itself upon initial seam detection.

9 Claims, 7 Drawing Figures

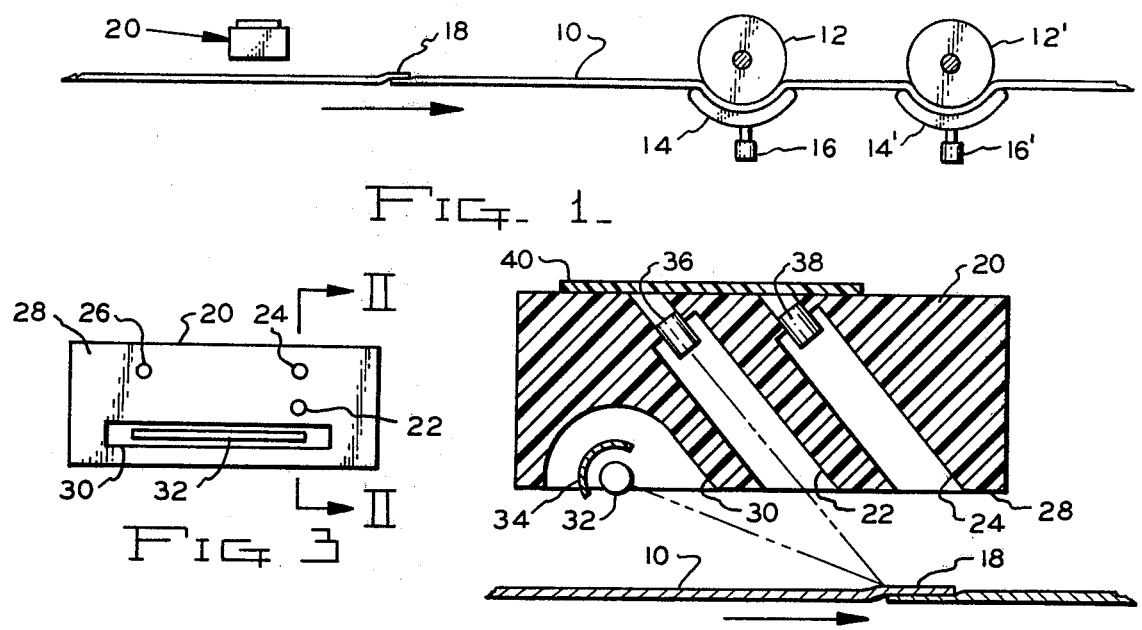
Fig. 1.
Fig. 3.
Fig. 2.
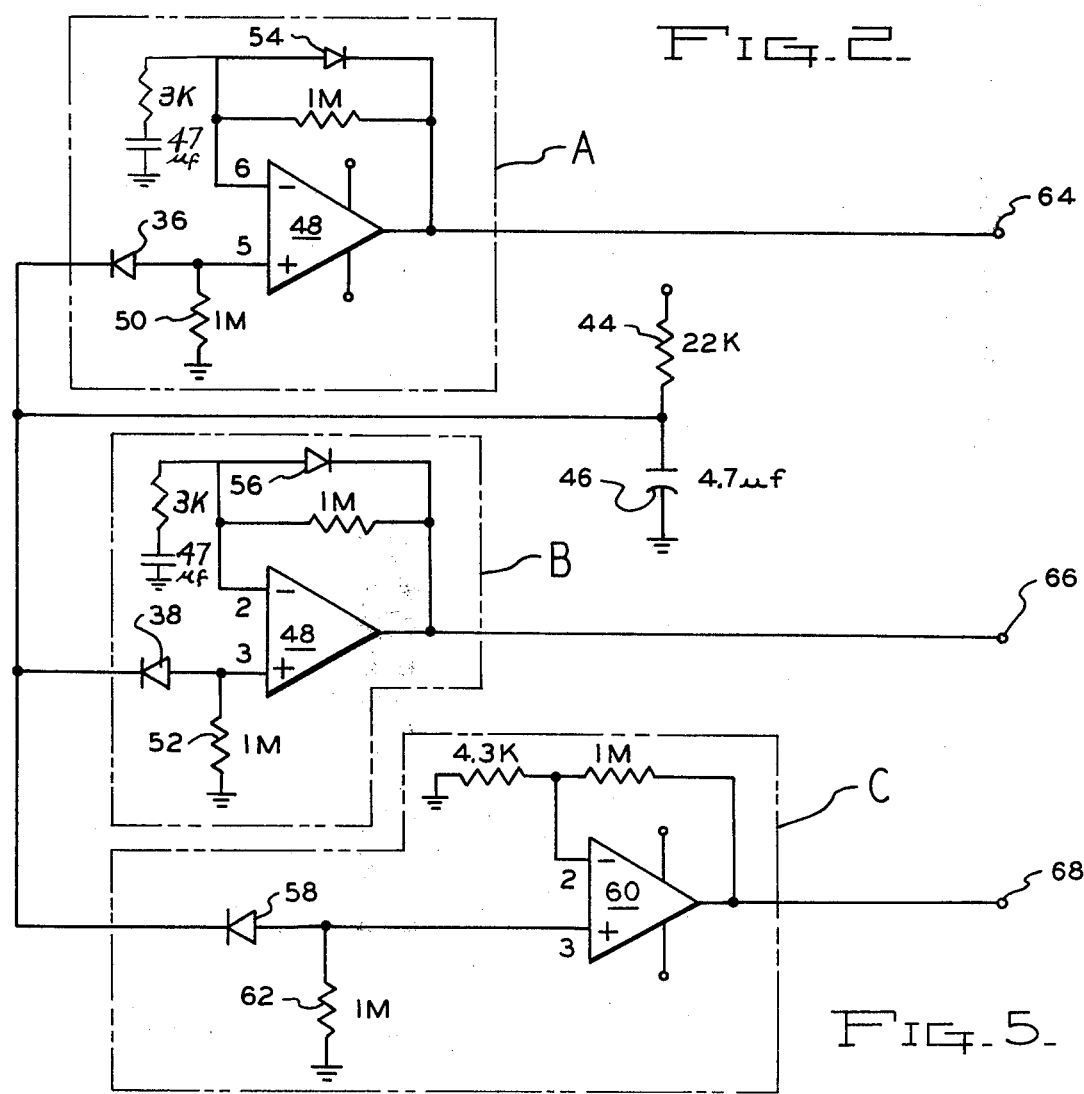
Fig. 5.

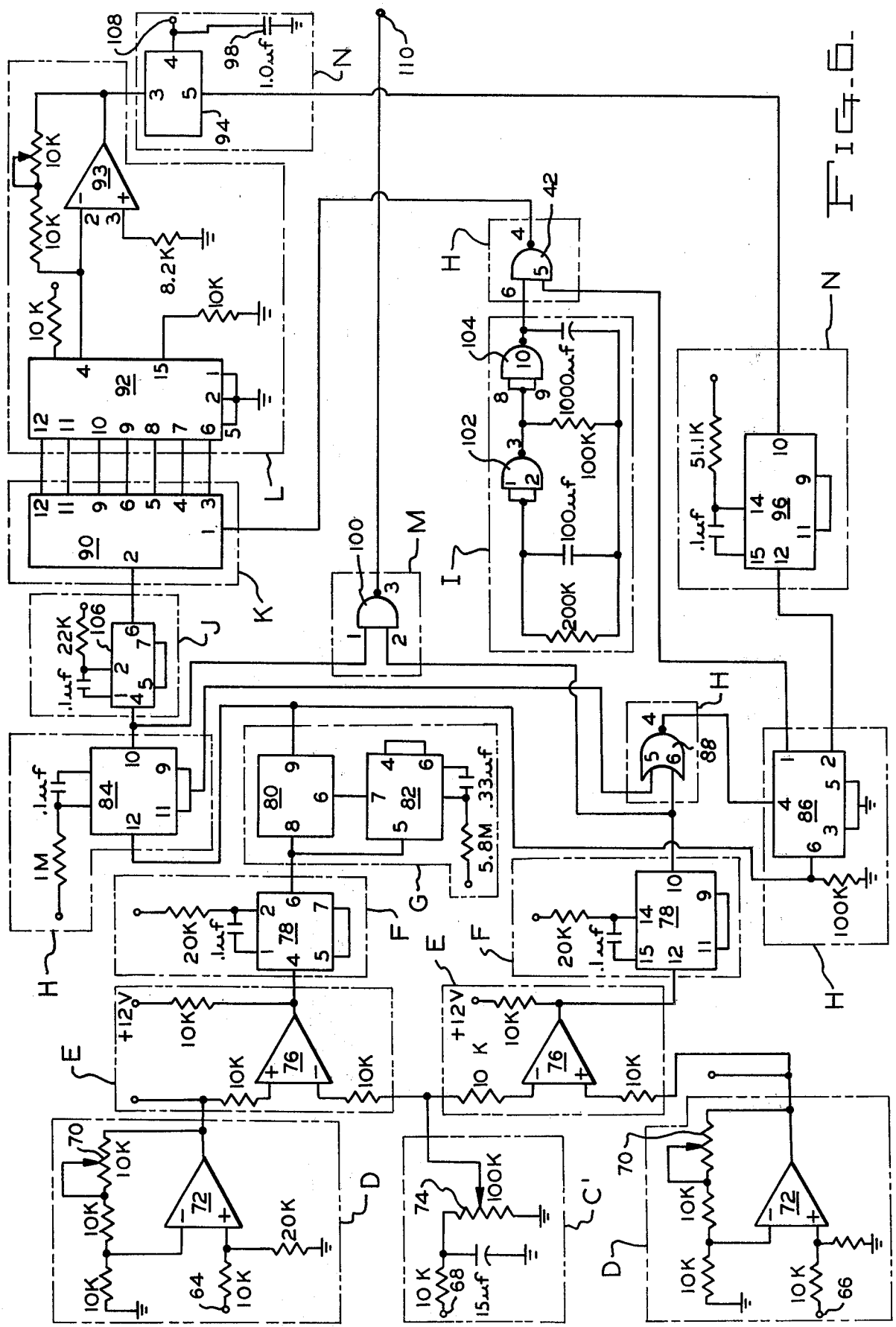

SEAM DETECTION AND CONTROL SYSTEM

BACKGROUND OF THE INVENTION

In continuous fabric finishing equipment strips of fabric are interconnected by seams, and as the fabric is processed the operator must be alert to the presence of a seam to avoid the seam adversely affecting the processing equipment.

For instance, in a common continuous finishing process of fabric drums and shoes are utilized to stress or compact the fabric. As the movement of a seam through the drums and shoes substantially increases the wear thereon it is common practice to "drop" the shoe as the seam moves through the drums in order to avoid the wear, and possible repair, that results from seam compression. With present fabric speeds the manual detection of seams is difficult, and high wear and maintenance costs are experienced in continuous finishing apparatus due to the inability of the operator to always detect a seam and modify the finishing equipment accordingly.

Fabric finishing equipment may also require that seams be removed from processed strips, and in seam removal apparatus of this type it has been necessary to manually detect the seam, and manually control the apparatus to properly locate the seam relative to the cutting apparatus, and such manual processing is expensive and time consuming.

Heretofore, difficulty has been encountered in the development of automatic seam detection and fabric control apparatus in that the rate of movement of the fabric in continuous fabric finishing apparatus varies greatly in dependence upon the nature of the processing, the fabric, the width of the fabric being processed, and other factors. While seam detection, and subsequent control of processing equipment, may be readily accomplished if the fabric movement is uniform, such variable velocities of fabric strip movement have previously thwarted the successful detection of seams and the subsequent control of processing apparatus.

It is an object of the invention to provide apparatus for detecting the presence of a seam in a strip of rapidly moving fabric, determining the rate of movement of the fabric, and controlling fabric processing equipment in accordance with the seam position relative thereto.

Another object of the invention is to provide apparatus for detecting the presence of a seam in rapidly moving fabric wherein subsequent processing apparatus located at a plurality of variable spaced positions may be timely actuated to accomodate the presence of the seam.

Yet a further object of the invention is to provide a detector for the presence of a seam in a rapidly moving fabric which is of an optical nature utilizing light reflected from the fabric, and wherein the light reflecting characteristics of the fabric are automatically compensated wherein uniform operation is achieved over a wide variety of fabric colors, and even patterns.

Another object of the invention is to provide a seam detection and control apparatus for rapidly moving fabric wherein false or "multiple" initiation of the control system due to inconsistencies in seam configuration are minimized.

In the practice of the invention a detector is located adjacent a rapidly moving web of fabric consisting of a plurality of fabric strips periodically sewn or otherwise affixed together defining a seam, and "behind" the detector with respect to the direction of fabric movement, fabric processing equipment is located which can be adversely affected by the seams and modification thereto is desired upon the seam arriving at such processing equipment. For instance, the fabric may be processed by drums and pressing shoes which stress or compact the fabric as it passes therebetween, and the passing of a seam between the drum and shoe imposes excessive wear thereon.

The detection of a seam is accomplished by an optical sensor wherein light cast upon the fabric face at the detector is reflected into a pair of sensors spaced with respect to each other in the direction of fabric movement. Thus, upon a seam passing under the detector an increased amount of light will be sequentially reflected unto the electronic light sensitive sensors producing two spaced electric signals wherein the duration between the signals represents the rate of movement of the seam, and fabric.

An automatic background control threshold voltage is imposed upon the circuit as determined by an optical sensor located at the detector receiving reflected light, and this threshold voltage is proportional to the reflectivity of the fabric, and modifies the circuit in accordance with the ability of the fabric to reflect light. This automatic background control assures uniform sensitivity and consistent operation with various fabric colors, and will also compensate for many colored patterns.

The spaced electronic signals produced by the detection of the seam initiate several electronic timers. The initial signal initiates the operation of a binary counter while the second signal terminates the counting thereof. Through a converter an analog voltage is produced inversely proportional to the velocity of the fabric movement. Further, the seam produced signal also initiates timing apparatus in the form of a ramp generator, and upon the ramp voltage equaling that produced by the binary counter a relay is tripped which controls the fabric processing equipment. For instance, the relay may actuate a valve mechanism for "dropping" a shoe away from a compressing drum in order to permit the seam to pass therethrough.

In the disclosed circuit two fabric processing stations are disclosed, and another timing circuit is initiated by the ramp generator circuit, which is also of the ramp generator type, wherein a second relay is actuated at a predetermined duration after the first relay whereby the shoe of the second compacting drum may be dropped.

As irregular seams may produce a plurality of signals due to variations in the light reflected thereby the circuit includes means for preventing multiple "start" signals from being imposed upon the circuit, and blanking means are incorporated into the circuit to provide uniform sensing and reduce the likelihood of improper circuit operation.

The seam detection and control system of the invention will detect seams in material traveling up to 250 yards per minute, there is no physical contact with the material, and the apparatus will properly function with both wet and dry fabric. Both overlapping and butt seams can be dependably sensed, and as the operation of the circuit is automatic, damage to fabric processing apparatus due to seams, as occurs with manual inspection, is eliminated.

BRIEF DESCRIPTION OF THE DRAWINGS

The aforementioned objects and advantages of the invention will be appreciated from the following drawings wherein:

FIG. 1 is a schematic, elevational, view of a typical fabric detection system in accord with the invention, FIG. 3 is an underside view of the seam detector, FIG. 5 is a circuit diagram of the detector components, and FIGS. 6 and 7 illustrate the circuit of the control system.

DESCRIPTION OF THE PREFERRED EMBODIMENT

The schematic illustration of FIG. 1 represents a typical environment with which the seam detection and control system of the invention is utilized. A strip or web of fabric is shown at 10, moving in the direction of the arrow. The invention finds particular use in apparatus for continuously finishing fabric, and such finishing may take a number of forms including stressing or compacting the fabric by the means of cylindrical drums 12 against which the fabric is compressed by shoes 14 of a concave configuration having an inner surface concentric to the associated drum. The shoe is moved upwardly toward the drum, or "dropped" away from the drum by an associated actuator 16 which may comprise a pneumatic or hydraulic expansible motor, or a mechanical apparatus such as a cam or the like. The actuator 16 is capable of very quickly dropping the shoe, and restoring it to its operable position adjacent the associated drum. In FIG. 1 two sets of drums and shoes are illustrated, the second set indicated by primed references, spaced apart in the direction of fabric movement about 36 inches, and the fabric passes under each drum and over the associated shoe wherein the fabric is compressed.

Figure 2:
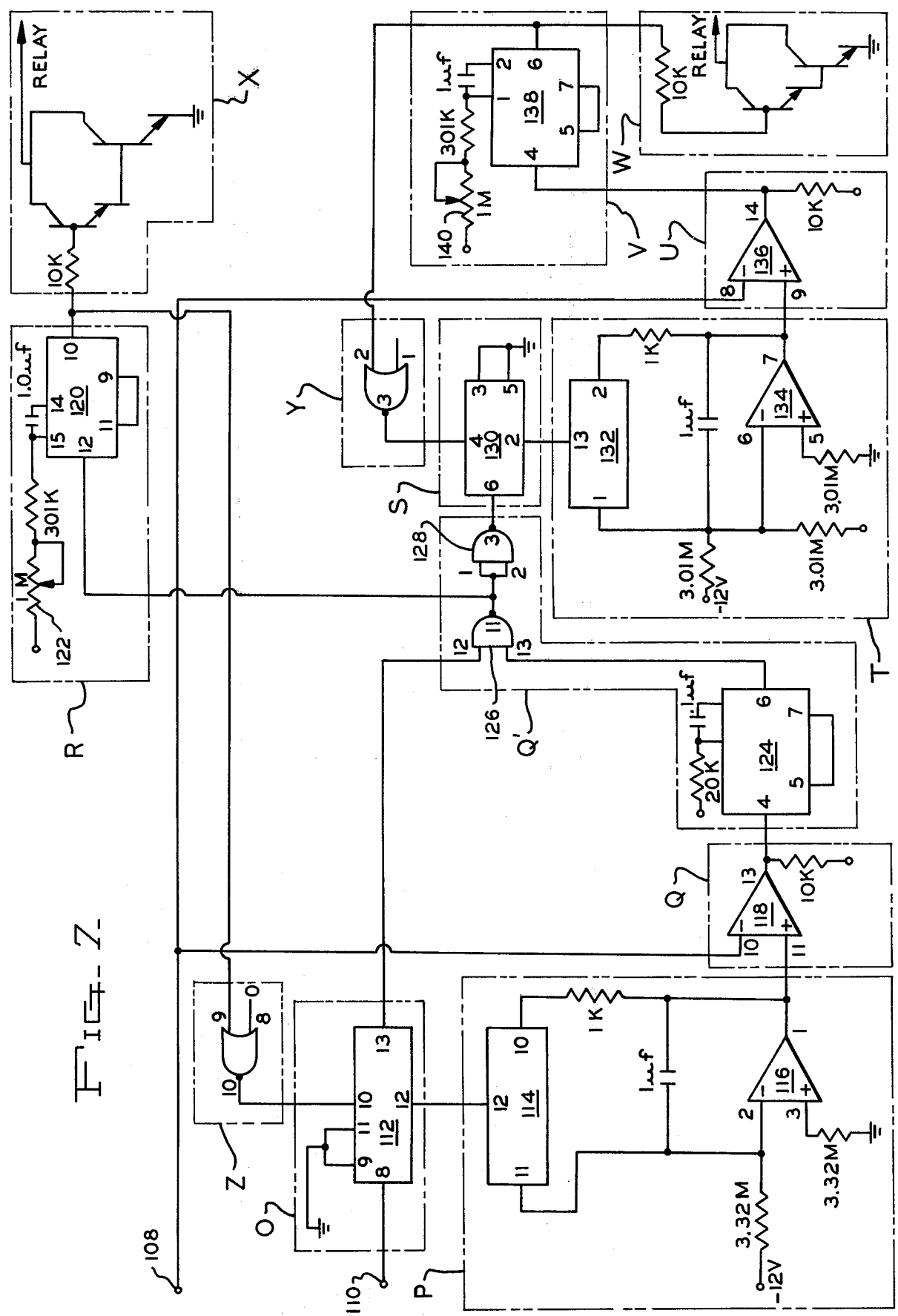
FIG. 2 is an elevational, sectional view taken through a detector along Section II—II of FIG. 3.

The fabric 10 being processed by the drums and shoes is formed of strips of material seamed together at their ends to form a continuous length. The seam, represented at 18, may be of the overlapping type as shown in FIG. 2, or of the butt type, and the seam may be formed by sewing or an adhesive. Usually, the thickness of the fabric strip at the seam will be greater, double in the case of an overlapping seam, than the usual fabric thickness, and if the seam passes between a compressing drum 12 and shoe 14 the increased seam thickness imposes significantly higher pressures between the drum and associated shoe causing wear thereon. Also, the presence of a seam between a drum and shoe substantially increases the frictional contact therebetween, and may result in damage to the fabric.

The basic purpose of the apparatus of the invention is to sense the arrival of a seam 18 at the fabric processing stations, such as the associated drums 12 and shoes 14, and modify the processing apparatus, such as sequentially dropping the shoes 14 and 14' as the seam sequentially engages the drums 12 and 12', respectively. As soon as the seam has passed the fabric processing apparatus the shoes are raised to continue fabric compaction.

The sensing of the seam 18 is accomplished by a detector 20 which may be disposed either above or below the fabric 10 a predetermined distance "ahead" of the drum 12, for instance 48 inches. The detector 20 is shown in the drawings in a basic configuration and includes a phenolic block in which three light receiving passages 22, 24, and 26 are formed, each intersecting the detector face 28 disposed toward the fabric. As appreciated in FIG. 2, the passages are obliquely oriented to the vertical, and the passage 24 is disposed "behind" the passage 22 a known distance, $\frac{1}{2}$ inch in most instances, in the direction of fabric movement.

The detector 20 also includes a recess 30 intersecting the face 28 and this recess includes a light source 32, and a reflector 34, wherein the fabric immediately opposed to the detector will be well illuminated, and light reflected from the fabric will enter the passages 22, 24 and 26.

A photo-diode sensor 36 is located at the end of passage 22, and a similar sensor 38 is located at the end of passage 24 wherein the sensors receive light entering the associated passages as reflected from the fabric. A cover plate 40 provides access to the sensors. As represented by the dotted lines of FIG. 2, the passing of the seam 18 past the detector 20 will first be detected by the sensor 36 and then by sensor 38 due to the increase of light reflected from the seam, as compared with that normally reflected from the fabric face.

The third passage 26 defined in the detector is identical to passages 22 and 24, and utilizes a similar photo-diode sensor, not shown, for producing a voltage proportional to the amount of light reflected upon the diode. The purpose of the passage 26, and associated sensor, is to establish a threshold voltage used to produce an automatic background control wherein the control circuit is automatically adjusted with respect to the particular light reflecting capabilities of the fabric being monitored. The automatic background control is explained in greater detail below.

In its basic operation, the detector 20 scans the adjacent fabric surface as it passes, and light reflected from the fabric face enters the passages 22 and 24, and is sensed by the sensors 36 and 38. The automatic background sensor imposes a threshold voltage on the circuit of the sensors wherein such usual reflected light does not creat a control signal, and the fabric processing proceeds in a normal manner wherein the drums 12 and associated shoes 14 will compact the fabric. Upon a seam 18 becoming aligned with passage 22, a substantially increased amount of light will be imposed upon the sensor 36, immediately producing an electric signal, and upon the seam being aligned with the passage 24 a second electronic signal is produced. The duration of time between the first and second electronic signals is evaluated to determine the rate of fabric movement, and as the detector 20 is a predetermined known distance proceeding the drum 12 with respect to the direction of fabric movement of detection of the seam, and the computation of its rate of movement toward the drum, permits the shoe 14 to be dropped from the drum upon the seam arriving at the drum. Further, as the spacing between the drums 12 and 12' is known, the shoe 14' may also be dropped from its associated drum 12' as the seam arrives thereat, and the sequential dropping of the shoes prevents excessive wear on the drums and shoes due to the presence of the seam and yet only that fabric immediately adjacent the seam is not processed by the drum and shoe sets. The circuit for accomplishing the above procedure is of a solid state and described below, and is reset upon the next seam being sensed by the detector.

Figure 4:
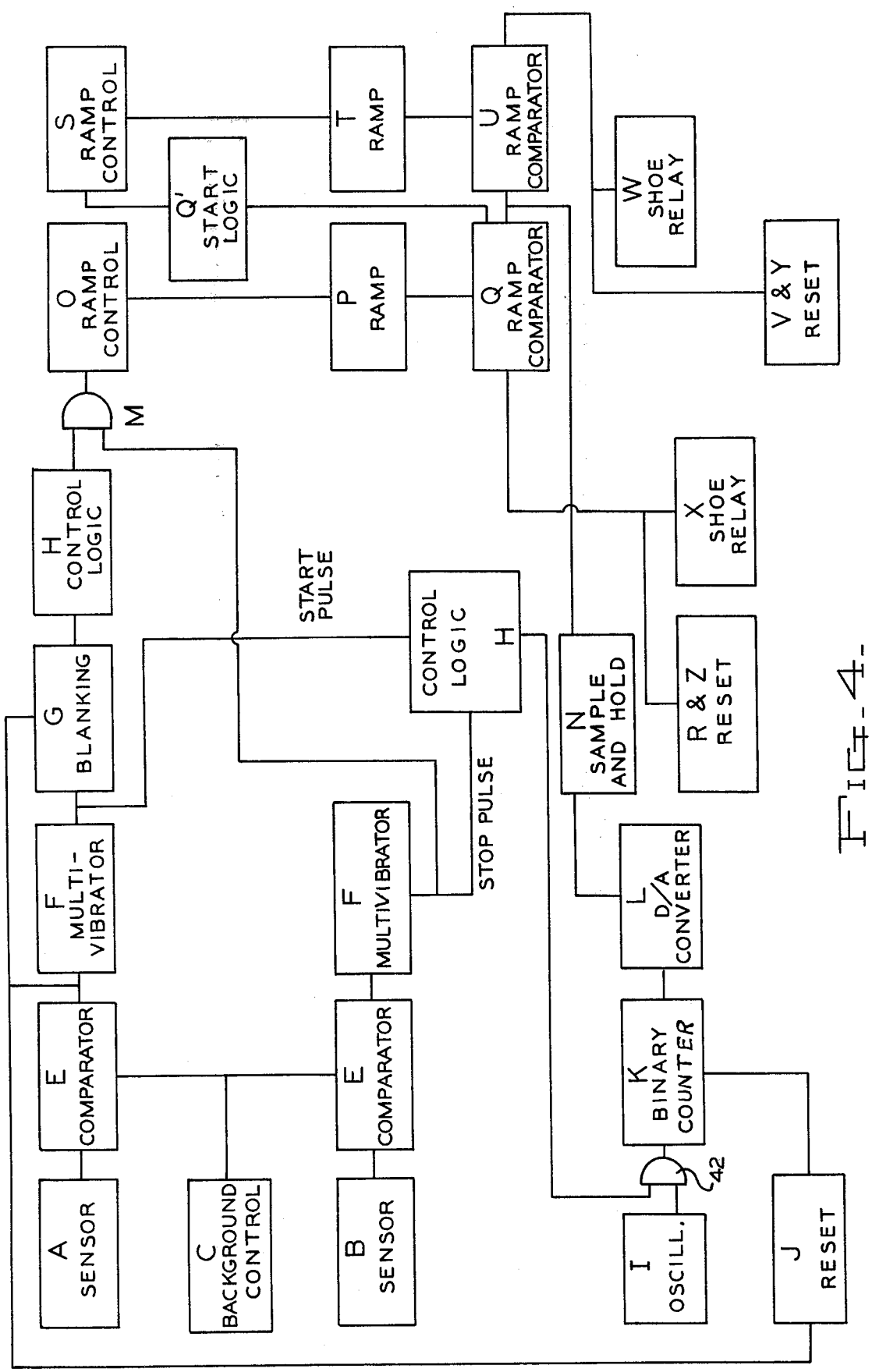
FIG. 4 is a schematic block diagram illustrating the basic components of the control circuit of the invention.

The general operation of the circuit of the invention will be appreciated from a description of the circuit block diagram of FIG. 4. In this block diagram portions of the circuit are identified by letter, and in the circuit diagrams of FIGS. 6 and 7 portions thereof corresponding to blocks illustrated in FIG. 5 are enclosed by dotted lines and identified by similar letters.

The sensor 36, A, and the sensor 38, B, have a normal low voltage output as the fabric face is being monitored, and the output of each sensor is connected to a dual voltage comparator E. The output of the background control circuit, C, is supplied to the comparators E, and the comparators are thereby supplied with a threshold voltage proportional to the degree of reflectivity of the fabric being monitored wherein a comparison can be made between the usual voltage output of the sensors, and the voltage output that occurs upon the detection of a seam. Upon a seam being detected by A and B a significantly higher voltage is fed to the associated comparator E. Due to the ½ inch separation between the detector passages 22 and 24 there will be a slight time interval between the "high" voltages impressed upon the comparators associated with sensors A and B, and the initial signal from A triggers a portion of a dual one shot multivibrator F which times out the voltage to produce a start pulse which is imposed upon the control logic for the counter as represented at H, and this control logic starts the binary counter K, which immediately begins the counting upon receiving the pulse generated at A.

Sensor B, upon sensing the seam, causes its associated comparator E to trigger the associated portion of one shot multivibrator F, and B produces a stop pulse which is supplied to the control logic H which stops the operation of the binary counter K. The binary count that has occurred at K is inversely proportional to the rate of fabric movement, i.e. the higher the count the slower the fabric velocity.

The output of counter K is supplied to 8 bit digital to analog convertor L, which provides a DC analog voltage proportional to the count of counter K.

As will be appreciated from FIG. 4, the stop pulse from sensor B, as well as being supplied to control logic H, is also fed to a quad AND gate M.

The AND gate M is also connected to the start pulse output at multi-vibrator F generated at sensor A, and this connection is through a blanking circuit G whose purpose is to prevent the circuit from malfunctioning if an unusually wide seam is detected, or the seam is of such form or reflectivity as to produce a plurality of rapid high outputs at sensor A. The blanking circuit senses the first pulse and blanks out subsequent pulses assuring that the circuit begins with the initial start pulse, and subsequent "high" voltages at sensor A are not imposed upon the circuit. Thus, in effect, circuit G blanks out voltage peaks originating at A which are extraneous to seam detection. The blanking circuit output is connected to the one shot multivibrator H which is part of the counter logic. The one shot circuit H will time out and wait until the stop pulse from sensor B has reached AND gate M. These two voltages are a logic which indicates sensors A and B have triggered, and it is now time to start processing the timer mechanism which determines when the seam will arrive at drum 12. The output of AND gate M is supplied to the control logic of a ramp generator consisting of the ramp control O, ramp P and ramp comparator Q. This ramp generator is usually held at zero volts and starts climbing to 12 volts at a slope which is preset depending upon the extent of the delay required, such as determined by the 48 inch separation between the detector 20 and the drum 12.

The output of the converter L is supplied to sample and hold circuit N whose function is to sample and hold the voltage output of converter L, and the output of circuit N is supplied to the ramp voltage comparator Q. Upon the ramp voltage equaling that resulting from counter K and held at N the ramp comparator output produces a voltage which energizes relay X which is connected to the actuator 16 of shoe 14, permitting the shoe to "drop" from its associated drum 12. Thus, it will be appreciated that the timing provided by the ramp circuit O, P and Q has been compared to the output of the binary counter K, which is inversely proportional to the fabric rate of movement, and the shoe 14 will be dropped upon the seam arriving at the drum 12.

The ramp comparator Q also supplies a dual one shot vibrator Q' connected to a second ramp control circuit as represented by blocks S, T and U. Thus, initiation of the second ramp circuit is from the first ramp timer circuit. The slope of the second ramp circuit will differ from that of the first ramp circuit in that the distance between the drums 12 and 12' is only 36 inches, rather than 48 inches, and upon the voltage at the second ramp comparator U equaling that produced by counter K and convertor L and held at N a second relay circuit W is energized which is connected to the second shoe actuator 16' causing the shoe to drop and permit the seam to pass therethrough.

The first ramp circuit O, P and Q is reset by the circuit represented in block R and Z, and the reset logic for the ramp circuit S, T and U is represented at block V and Y.

With reference to FIG. 4, it will also be noted that the binary counter K is supplied by the 4K $H_z$ oscillator I through N AND gate 42, and resetting of the binary counter is through the reset circuit J connected to the output of the comparator E associated with sensor A.

The circuitry immediately associated with the detector 20 is shown in FIG. 5. Photo-diode sensors 36 and 38 are of the OP-803 type and are reverse biased by resistor 44 and condensor 46 to assure linear operation. The circuits associated with the sensors 36 and 38 are identical and each utilizes an AC amplifier 48, and the output of each amplifier are equal for a given seam. The passages 22 and 24 which receive the reflected light are obliquely disposed to the horizontal and, actually, receive little reflected light, and the output of the associated amplifiers are between 100 and 500 mv. When a seam passes the detector and the amount of light sensed by the sensors increases, the DC voltage at resistors 50 and 52 typically increases by 5–20 mv, and this change is amplified to give an output of 2–10 volts. This wide range of output is due to the fact that some fabric seams reflect more light than others. Diodes 54 and 56 prevent the amplifier outputs from going negative as would occur if a hole in the fabric passes the viewing area.

The photo-diode sensor 58 is located at the end of the detector passage 26, and also is of the OP-803 type, and this sensor is used to establish the DC reference voltage of the automatic background control. The output of sensor 58 is fed to dual voltage comparator 60, and sensor 58 is reverse biased by resistor 44 and condenser 46 to provide linear operation. Light reflected from the fabric is converted into a DC voltage across resistor 62, and sensor 58 operates as a constant current source with a linear output related to the amount of light it is receiving. This system establishes a threshold voltage which will linearly track over a wide range of material with different degrees of reflectivity.

With reference to FIG. 6, the output of sensor A is connected to a buffer circuit shown in block D, and the output of sensor B is connected to a similar buffer amplifier circuit, and the purpose of these buffer amplifier circuits 72 is to amplify the signal and adjust the sensors for equal output so that the same output will be generated for a given seam. The adjustment is accomplished by the resistors 70.

The output of the automatic background control circuit C of FIG. 5 is connected to the background control adjusting circuit C' of FIG. 6. This circuit in FIG. 6 forms a low pass filter for removing the AC component to produce a clean DC signal. Resistor 74 is used to set the threshold for a particular value.

The output of the buffer amplifiers D is supplied to the voltage comparator circuits 76 at E, who in turn, are connected to the one shot multi-vibrators 78 at F. As described above, the output of the multi-vibrator 78 connected to sensor A is supplied to the blanking circuit G which includes a quad bilateral switch 80 and multi-vibrator 82, and the start pulse is supplied to the control logic H. The electric signal received from sensor B initiates the stop pulse from its associated multi-vibrator 78 which is also fed into the control logic H. The control logic H also functions to stop the counter if a stop pulse has not been received, as may occur if, for some reason, a second reflected signal from the seam is not produced. The control logic H includes multi-vibrator 84, dual D-type flip/flop 86, OR gate 88 and NAND gate 42.

From the circuit the interconnection of control logic H, binary counter 90 at K, and digital to analog convertor 92 at L which includes amplifier 93, will be appreciated. As previously mentioned, a DC analog voltage is produced at the output of the converter L, and this output is supplied to the sample and hold quad bilateral switch 94 and multi-vibrator 96 constituting circuit N. This circuit momentarily connects the output of converter L to capacitor 98, and the length of such connection is determined by one shot multi-vibrator 96. Thus, the capacitor 98 stores a voltage inversely proportional to the fabric velocity.

The oscillator circuit I for the binary counter 90 includes quad NAND gates 102 and 104 to provide a 4K $H_z$ oscillation at the counter, and the counter reset circuit J includes the dual one shot multi-vibrator circuit 106 for resetting the counter upon a new seam being sensed.

The quad AND gate 100 at M is connected to a D-type flip/flop 112 at circuit O, and upon a pulse being received from gate 100 the control logic of ramp generator O, P and Q begins. Circuit O is connected to the combination bilateral switch 114 and operational amplifier circuit 116 at P, and the ramp comparator circuit Q is connected to the sample and hold circuit N at the negative input of the quad voltage comparator 118.

The circuit Q', and the circuit R, serve several purposes. Circuit R is part of the circuit which resets the first ramp circuit, and the circuit Q' is the circuit which initiates the second ramp circuit S, T and U. The circuit R includes multi-vibrator 120 and resistor 112, can be adjusted to determine how long the relay circuit X will be actuated, thereby determining the length that the shoe 14 will be dropped.

With reference to FIG. 7, circuit Q', through multi-vibrator 124, NAND gate 126 and inverter 128 initiates the second ramp control circuit by its input into D-type flip/flop 130 at circuit S, bilateral switch 132 and operational amplifier 134 at circuit T and voltage comparator 136 at circuit U. The resetting of this ramp circuit, and the length of time that the shoe 14' will be dropped, are accomplished through circuit V which includes multi-vibrator 138, and resistor 140 which control actuator relay W, and resetting includes OR gate 142 of circuit Y.

The relay circuits X and W include transistors of the NPN type as manufactured by RCA, number 2N2222A, and provide a sufficient control current to operate the associated shoe actuator relay control.

As will be appreciated, the entire control circuit is solid state electronics, and highly dependable in operation. Fabric velocities up to 150 yards per minute can be monitored on either wet or dry fabric, and the fact that the shoes will be dropped only long enough to permit the seam to pass insures that consistent processing of a maximum amount of fabric will occur, while minimizing wear due to passing of seams through the processing apparatus.

It is to be appreciated that the fabric processing apparatus with which the seam control is utilized may differ from the drums and shoes illustrated. For instance, fabric processing wherein the seam is to be removed from the fabric strip can utilize the inventive concepts of the invention, as well as apparatus which visibly marks the seam location, or otherwise indicates where seam processing is to occur.

The integrated circuits and components illustrated in the drawings are of conventional commercial availability, and manufacturers and model numbers are identified below:

| Reference Number | Manufacturer | Model Number |
| --- | --- | --- |
| 48,72 | National Semiconductor | LM 1458A |
| 60,76 | National Semiconductor | LM 393N |
| 93 | National Semiconductor | LM 1458N |
| 118,136 | National Semiconductor | LM 339N |
| 92 | Precision Monolithics Inc. | DAC-08CQ |
| 116,134 | Texas Instruments | TL 072 CP |
| 78,82,84 | RCA | CD 4098 BE |
| 80,94,114,132 | RCA | CD 4016 BE |
| 88 | RCA | CD 4071 BE |
| 86,112,130 | RCA | CD 4013 BE |
| 96,106,120,124, 138 | RCA | CD 4098 BE |
| 90 | RCA | CD 4024 BE |
| 100 | RCA | CD 4081 BE |
| 42,102,104,126 | RCA | CD 4011 BE |
| 128 | RCA | CD 4093 BE |

It is appreciated that various modifications to the inventive concepts may be apparent to those skilled in the art without departing from the spirit and scope of the invention. For instance, while the invention is described as used with seam detection in textile fabrics, the term "fabric" is to be broadly defined and the inventive concepts may be employed with webs or strips of rubber, plastic or other materials wherein a seam or other variation in the strip is to be detected.

I claim:

1. A seam detection and control system for fabric processing apparatus processing a strip of moving fabric having spaced seams comprising, in combination, a detector located adjacent the moving fabric strip, sensing means mounted upon said detector producing first and second electronic signals upon a seam passing said detector separated by a time duration proportional to the velocity of movement of the seam past the detector, first fabric processing means processing the fabric at a predetermined location behind said detector with respect to the direction of fabric movement and having first and second processing conditions, first actuating means associated with said first fabric processing means selectively shifting said processing means between said first and second conditions, a first electronic timer connected to said sensing means and producing a first control signal having characteristics determined by the time duration between said first and second signals indicating the velocity of movement of the fabric, and a second electronic timer controlling the operation of said first actuating means between said first and second conditions producing a second control signal determined by the distance between said detector and said first fabric processing means receiving and evaluating said first control signal and energizing said actuating means upon a seam arriving at said first fabric processing means as determined by a comparison of said first and second control signals.

2. In a seam detection and control system as in claim 1, wherein said second timer receives said first and second electronic signals from said sensing means and is initiated thereby.

3. In a seam detection and control system as in claim 2, wherein said first timer comprises a binary counter and said first control signal comprises a voltage having a value inversely proportional to the fabric velocity.

4. In a seam detection and control system as in claim 3, wherein said second timer includes a ramp generator and said actuating means is energized upon the voltage of said second control signal of the ramp generator becoming equal to the voltage of said first control signal.

5. In a seam detection and control system as in claim 1, second fabric processing means processing the fabric at a predetermined location behind said first fabric processing means with respect to the direction of fabric movement and having first and second processing conditions, second actuating means associated with said second processing means selectively shifting said second processing means between its first and second conditions, and a third electronic timer controlling the operation of said second actuating means between its first and second conditions producing a third control signal determined by the distance between said first and second fabric processing means receiving and evaluating said first control signal and energizing said second actuating means upon a seam arriving at said second fabric processing means as determined by a comparison of said first and third control signals.

6. In a seam detection and control system as in claim 5, wherein said second electronic timer is connected to said third electronic timer and initiates said third timer.

7. In a seam detection and control system as in claim 6, wherein said third timer includes a ramp voltage generator and said second actuating means is energized upon said ramp generator third signal voltage of said third timer becoming equal to the voltage of said first control signal.

8. In a seam detection and control system as in claim 1, automatic background control means located adjacent the strip of moving fabric sensing the light reflecting characteristics of the fabric, said sensing means comprising light sensors, and means connecting said background control means to said sensing means whereby said background control means adjusts said sensing means with respect to the particular light reflecting characteristics of the fabric being sensed.

9. In a seam detection and control system as in claim 1, blanking means connected to said first sensor receiving said first electronic signal, said blanking means disregarding subsequent signals received from said first sensor after reception of said first signal until the control system is reset.

* * * * *